(12) United States Patent
Mann (10) Patent No.: US 6,520,936 B1
(45) Date of Patent: Feb. 18, 2003

(54) METHOD AND APPARATUS FOR INFUSING LIQUIDS USING A CHEMICAL REACTION IN AN IMPLANTED INFUSION DEVICE

(75) Inventor: Alfred E. Mann, Northridge, CA (US)

(73) Assignee: Medtronic Minimed, Inc., Northridge, CA (US)

(*) Notice: Subject to any disclaimer, the term of this patent is extended or adjusted under 35 U.S.C. 154(b) by 198 days.

(21) Appl. No.: 09/590,482

(22) Filed: Jun. 8, 2000

Related U.S. Application Data (60) Provisional application No. 60/138,138, filed on Jun. 8, 1999.

(51) Int. Cl.⁷ .................................................. A61M 37/00
(52) U.S. Cl. .................................... 604/141; 604/891.1
(58) Field of Search .......................... 604/141, 93, 131, 604/140, 19; 128/899

(56) References Cited

U.S. PATENT DOCUMENTS

| | | | |
|---|---|---|---|
| 3,702,532 A | | 11/1972 | Low et al. |
| 3,894,538 A | | 7/1975 | Richter |
| 4,639,244 A | * | 1/1987 | Rizk et al. .................. 604/19 |
| 4,687,423 A | | 8/1987 | Maget et al. |
| 4,759,527 A | | 7/1988 | Brown |
| 4,886,514 A | | 12/1989 | Maget |
| 4,902,278 A | | 2/1990 | Maget et al. |
| 5,135,498 A | * | 8/1992 | Kam et al. .................. 604/140 |
| 5,318,540 A | * | 6/1994 | Athayde et al. ............ 604/141 |
| 5,492,534 A | * | 2/1996 | Athayde et al. ............ 604/141 |
| 5,538,605 A | | 7/1996 | Gordon et al. |
| 5,954,058 A | * | 9/1999 | Flaherty ...................... 128/899 |
| 5,957,890 A | * | 9/1999 | Mann et al. ................. 604/131 |
| 6,048,328 A | * | 4/2000 | Haller et al. ................. 604/93 |
| 6,280,416 B1 | * | 8/2001 | Van Antwerp et al. ..... 604/141 |
| 6,283,943 B1 | * | 9/2001 | Dy et al. ..................... 604/141 |

FOREIGN PATENT DOCUMENTS

| | | |
|---|---|---|
| DE | 36 21 846 | 1/1988 |

* cited by examiner

*Primary Examiner*—Teresa Walberg
*Assistant Examiner*—Leonid M Fastovsky
(74) *Attorney, Agent, or Firm*—Foley & Lardner (57) ABSTRACT

Embodiments of implantable infusion pumps are provided that use a process of converting a first substance to a second gaseous substance (e.g. by electrolysis) to provide a motivating force to expel a desired fluid (e.g. drug or medication) from the pump into the body of a patient. An expandable sack may be provided around a gas producing electrolytic cell, such that as the gas expands it displaces a portion of the volume originally allocated to the desired fluid, and thereby forces the fluid from the pump. Pumps may be provided with a double septum to allow refilling of the desired fluid while simultaneously allowing removal of the generated gas from the system while using a single needle. Recharging of pump batteries may occur by direct electrical conduction through one or more needles and/or by r.f. energy transfer. Programming of the pump may occur by way of conductive paths provided by one or more needles or by means of r.f. transfer. A pressure regulator may be provided in vicinity to an outlet port of the pump so as to enable more reliable operation of the pump when subjected to changes in ambient pressure. A one-way valve may also be provided to reduce risk of back flow into the pump.

40 Claims, 9 Drawing Sheets

METHOD AND APPARATUS FOR INFUSING LIQUIDS USING A CHEMICAL REACTION IN AN IMPLANTED INFUSION DEVICE

PRIORITY CLAIM

This application claims benefit to U.S. Provisional Patent Application Serial No. 60/138,138, filed Jun. 8, 1999, which is hereby incorporated by references as if set forth herein in full.

FIELD OF THE INVENTION

This invention relates to implantable infusion pumps for controlled delivery of a selected infusant and more particularly to implantable infusion pumps that generate volumes of gas that are utilized in administering desired quantities of a selected fluid to a patient (i.e. a person or animal being treated or benefited by the fluid).

BACKGROUND OF THE INVENTION

Implantable infusion pumps currently utilize either an active electromechanical pump or a gas propellant driven "constant flow" system. The former devices are generally programmable and use a battery and electronic circuitry to cause a rotary peristaltic pump or a piston pump to deliver a selected fluid (e.g. drug, medication, or protein) that is stored in a reservoir according to a preset delivery profile or one that can be set by the patient or a health care professional. An example of such a device is found in U.S. Pat. No. 4,573,994 to Fischell. This patent is hereby incorporated herein, in full, by this reference.

The latter devices are currently non-programmable and deliver the fluid at an essentially constant rate by driving a bellows reservoir with pressure created by a propellant such as FREON. An example of such a device is found in PCT publication WO 98/56443, to Mann, et al., published Dec. 17, 1998. This PCT application claims priority to U.S. patent application Ser. No. 08/871,830, filed on Jun. 7, 1997. This PCT publication and U.S. patent application are hereby incorporated herein, in full, by this reference.

A need exists in the art for pumps with improved features such as reduced size, and/or reduced cost.

SUMMARY OF THE INVENTION

It is a first object of selected embodiments of the present invention to provide a an implantable infusion system of reduced size.

It is a second object of selected embodiments of the present invention to provide an implantable infusion system having reduced cost.

A first aspect of the invention provides an implantable infusion pump for dispensing a fluid to a patient, including: (1) a pump housing capable of being implanted in a body of a patient; (2) an inlet in the housing for receiving the fluid to be dispensed; (3) an outlet in the housing from which fluid is dispensed; (4) a first reservoir of variable size for holding the fluid, wherein the inlet and first reservoir are at least periodically connected by a flow path so as to allow fluid supplied to the inlet to flow to the first reservoir, and wherein the outlet and first reservoir are at least periodically connected by a flow path so as to allow fluid in the first reservoir to be dispensed through the outlet; (5) a second reservoir of variable size for holding a gas; (6) a volume comprising the first reservoir and the second reservoir, such that as the second reservoir expands in size the first reservoir diminishes in size; and (7) a gas generating source for controllably and variably producing quantities of gas that expand the size of the second reservoir, thereby decreasing the size of the first reservoir to cause dispensing of fluid through the outlet to the patient.

A second aspect of the invention provides a method for infusing a fluid into a body of a patient, including: (1) providing an implantable device in a patient, wherein the implantable device includes a volume that is partitioned into a first reservoir of variable size and a second reservoir of variable size, such that as the second reservoir expands in size the first reservoir diminishes in size; (2) providing fluid to a first reservoir; and (3) generating and providing within the implantable device quantities of a gas on a controllable and variable basis to the second reservoir to cause expansion of the second reservoir such that a portion of a volume of the first reservoir is diminished and a portion of the fluid originally supplied to the first reservoir is dispensed through an outlet of the implanted device into the body of the patient.

A third aspect of the invention provides an implantable device for dispensing a drug to a patient, including: (1) a means for holding a fluid that may be electrolyzed; (2) a means for causing a selected amount of the fluid to be electrolyzed to produce a gas; (3) a means for separating produced gas from the fluid and allowing the gas, but not the fluid, to pass to a volume surrounded by a variable size containment means; (4) a reservoir means for holding a drug to be dispensed, the reservoir means being of variable size and located in relation to the containment means such that as the containment means increases in size the reservoir means decreases in size thereby dispensing the drug to the patient; (5) a means for refilling the reservoir with the drug; and (6) an means to remove gas from inside the containment means so that refilling of the reservoir means may occur.

While certain objectives and aspects of the invention have been noted above, other objectives and aspects will be apparent to those of skill in the art upon study of the teachings herein. It is not required that each aspect of the invention simultaneously address all of the objectives of the various embodiments. Each aspect of the invention may address a single one of the objectives or alternatively might address a combination of two or more objectives.

Embodiments of the invention provide implantable infusion pumps that use a process of converting at least one chemical substance (first chemical substance) to at least one gaseous substance (second chemical substance), e.g. by electrolysis, to provide a motivating force to expel a desired fluid (e.g. drug, medication, or protein) from the pump into the body of a patient.

Some embodiments provide an expandable sack around a gas producing electrolytic cell, such that as the gas expands it displaces a portion of the volume originally allocated to the desired fluid, and thereby forces the fluid from the pump.

Some embodiments provide pumps with a double septum to allow refilling of the desired fluid while simultaneously allowing removal of the generated gas from the system while using a single needle.

Some embodiments provide recharging of pump batteries by direct electrical conduction through one or more needles and/or by inductive or radio frequency energy transfer.

Some embodiments provide programming of the pump by way of conductive paths provided by one or more needles or by means of inductive or radio frequency transfer.

Some embodiments provide a pressure regulator in the vicinity of an outlet port of the pump so as to enable more reliable operation of the pump when subjected to changes in ambient pressure.

Some embodiments provide a one-way valve to reduce risk of back flow into the pump.

BRIEF DESCRIPTION OF THE DRAWINGS

Preferred embodiments of the invention are described with the aid of the accompanying figures.

DESCRIPTION OF PREFERRED EMBODIMENTS OF THE INVENTION

Figure 1:
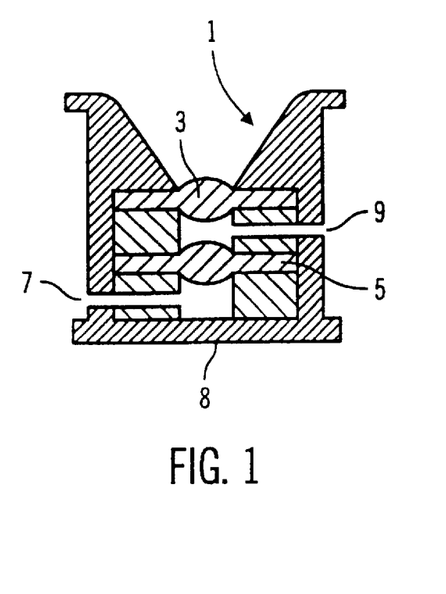
FIG. 1 illustrates a filling port for use in a preferred infusion pump.
Figure 3A:
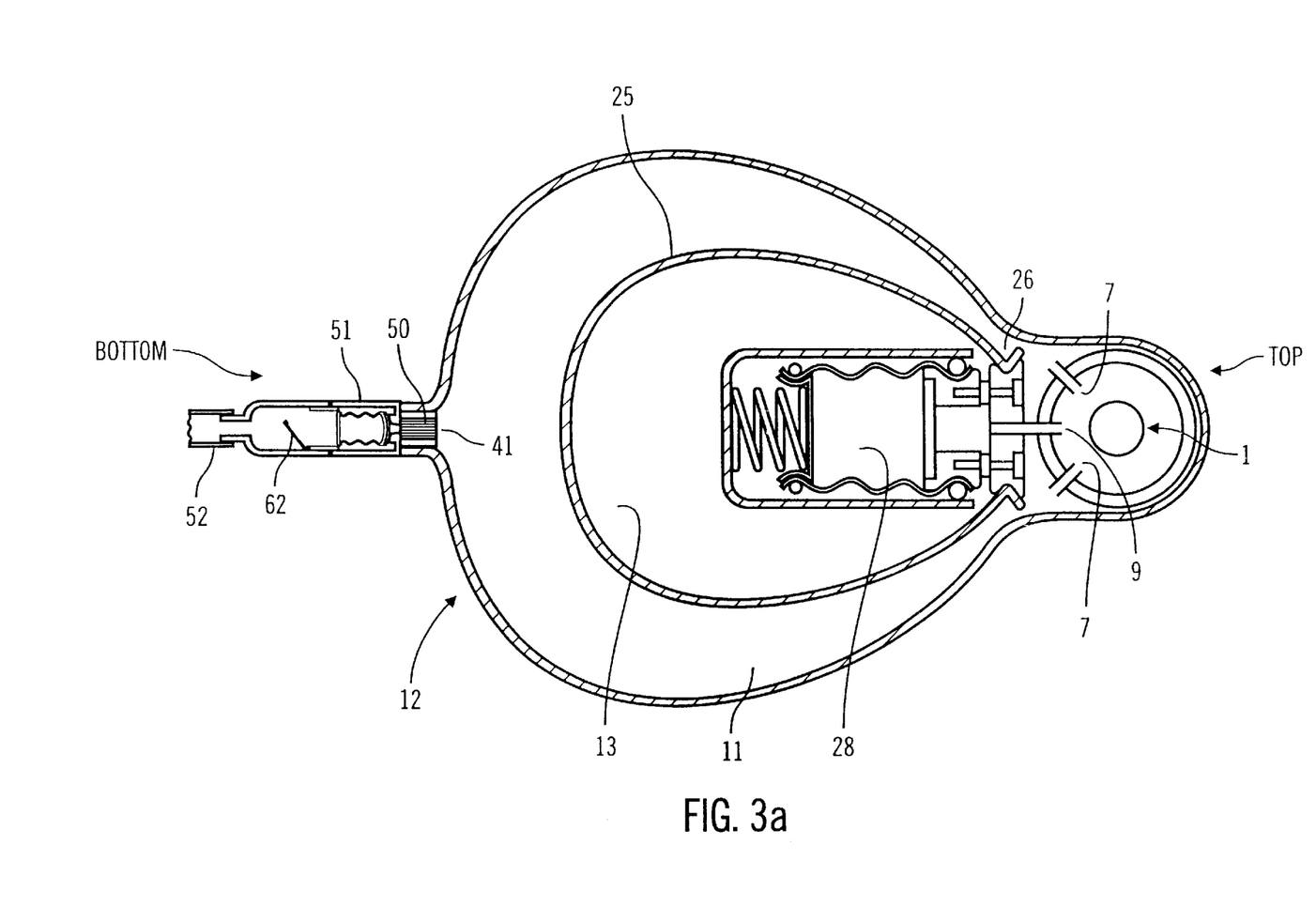
FIGS. 3a and 3b show a preferred pump assembly according to a preferred embodiment of the invention.
Figure 3B:
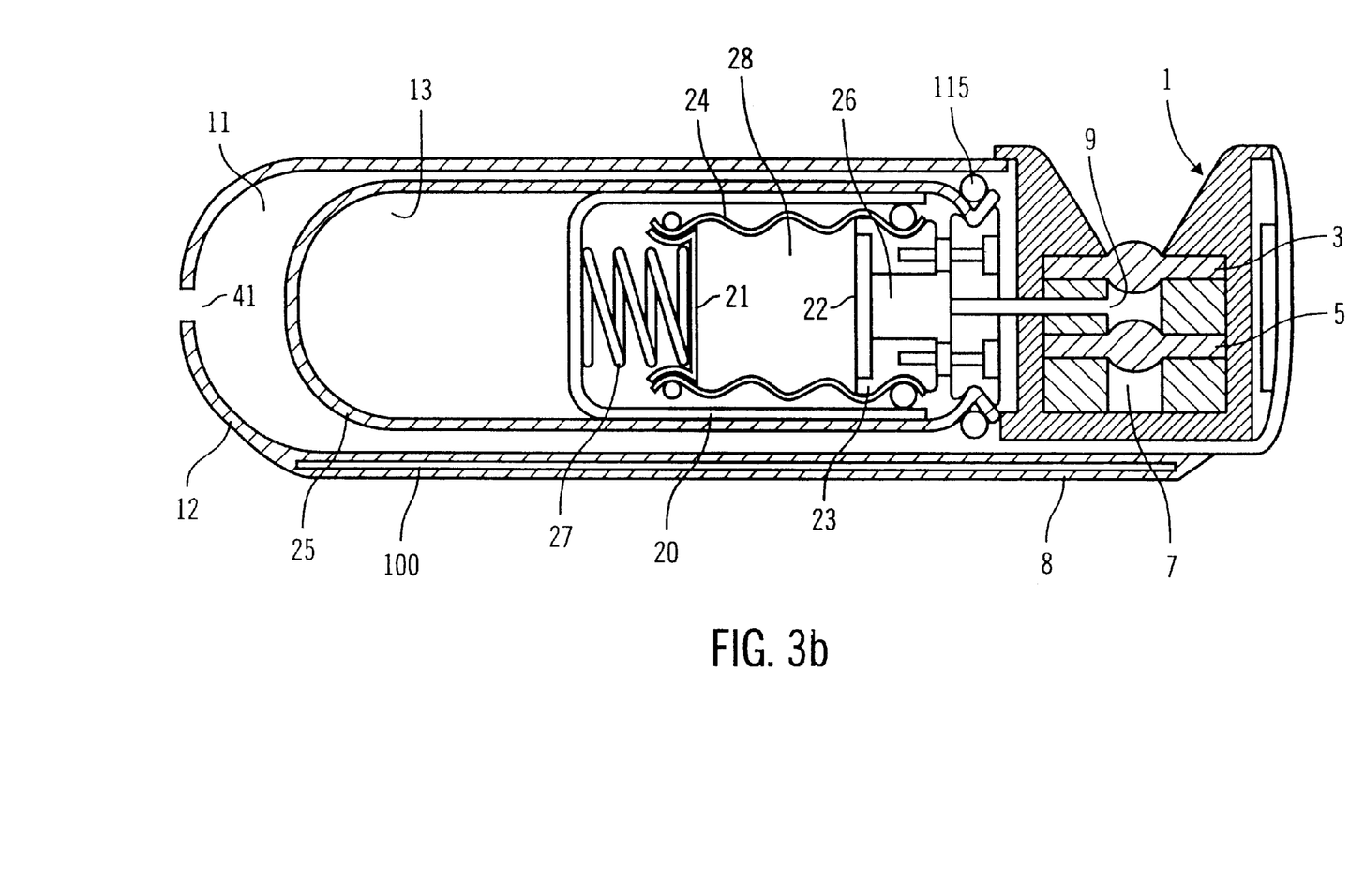
Figure 4:
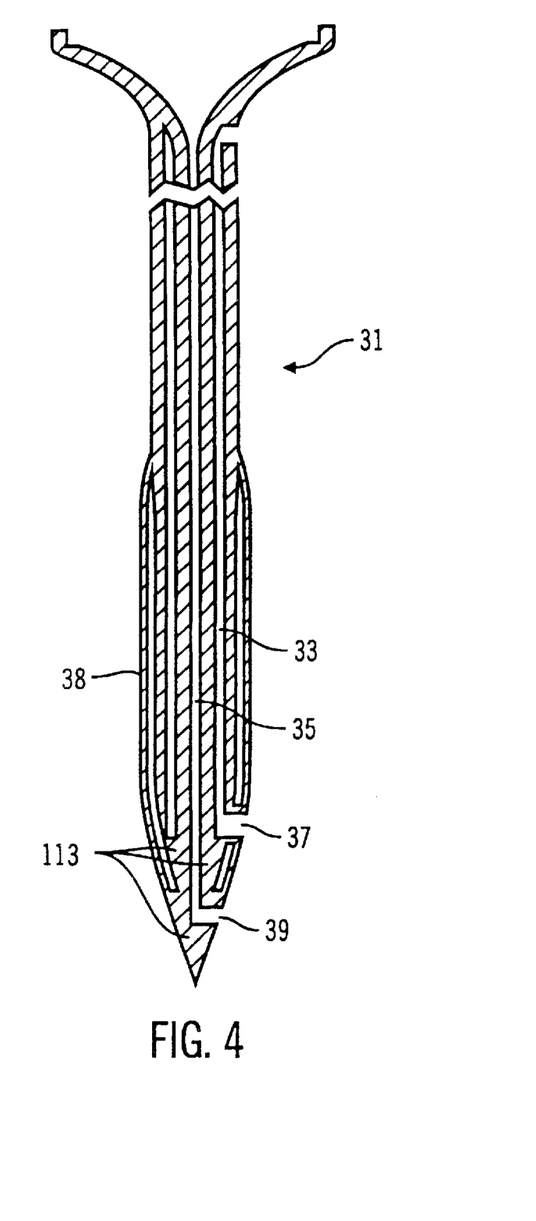
FIG. 4 illustrates a coaxial twin lumen needle used for filling a pump reservoir with medication in a preferred embodiment.

FIG. 1 illustrates a preferred inlet for an infusion pump system that uses a gas propellant to force infusant from an outlet of the system. The preferred filling port includes a conical inlet area 1 and a first septum 3. However, rather than a valve to seal off the reservoir, as known in the art, there is a second septum 5 with a further space below it. Between the first septum 3 and the second septum 5 is a gas port 9 that is functionally connected to the inside of the propellant chamber 13 (i.e. a second reservoir) shown in FIGS. 3a and 3b, so that gases contained in the propellant chamber 13 can be exhausted from the system when a special needle 31, such as that shown in FIG. 4, is properly inserted into the inlet port. Beyond the second septum 5 is a port 7 in the inlet housing that communicates with the fluid (e.g. drug or medication) reservoir 11 (i.e. a first reservoir) of FIGS. 3a and 3b, and below that is a stop 8. To fill the reservoir 11, the needle 31 of FIG. 4 is inserted into the inlet port 1 such that the needle bottoms out against the stop 8. The gas outlet 37 of the needle is then located between the septums 3 and 5, and the liquid outlet 39 is between the second septum 5 and the stop 8. To fill the reservoir 11, gases are exhausted through the outer lumen 33 of the needle 31 and the medication flows into the reservoir 11 through the inner lumen 35. The filling can be done by pushing the liquid through the needle, thereby forcing the gas out. Alternatively, and possibly with enhanced safety, the gas may be forcibly extracted so that the medication is drawn into the reservoir 11. In a further alternative, the ports in the inlet chamber and needle may be reversed. In a further alternative separate inlet ports may be accessed by separate fluid and gas needles. The separate ports may be of different sizes and thus provide differential accessibility to different sized fluid and gas needles.

FIG. 4 is an illustration of a needle 31 that may be used to fill the reservoir. Such a needle 31 may be made by inserting a small needle with a hole on the side near the tip (e.g. a Huber needle that is cut off slightly below the hole) into a larger needle with two side ports. The tip may be potted up to the opening 37, as shown at 113, except for a path between the inner needle side port and the distal port of the outer needle, creating a path from the inner cannula to the outside. The edges of the lower portion of this needle 31 on the outside must be smooth so that the septums are not damaged when needle 31 is inserted into or extracted from these septums.

Figure 2:
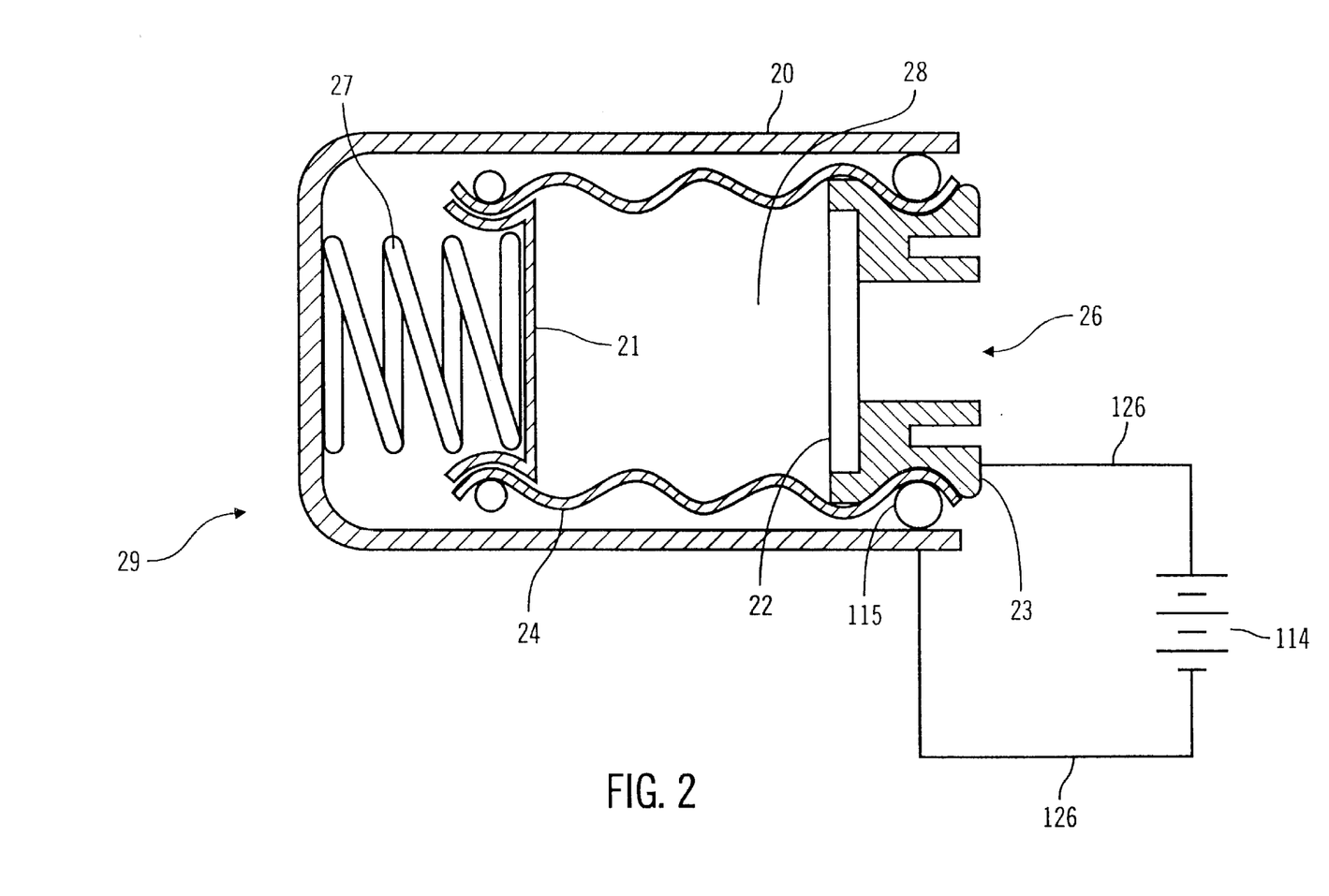
FIG. 2 illustrates an electrolytic cell for generating a gas that is used to force medication from an embodiment of a preferred infusion pump.

A pump according to a first preferred embodiment of this invention uses electrolysis of a liquid to convert a first chemical substance to a second substance to form a volume of gas within an electrolytic cell 29 that in turn causes medication infusion by creating a pressure on the medication in reservoir 11 to exceed a pressure required for dispensing. In this embodiment as shown in FIG. 2, the electrolytic cell 29 has a frame 20 with an electrode 21 (e.g. a plate or cup) sealing one end and a membrane 22 at the other end. The membrane is positioned (e.g. stretched) across a ring 23 that defines the second end of the cell. An elastomeric tube or bellows 24 (e.g. plastic is good enough) is attached between the ring 23 and the electrode 21 (e.g. cup). The elastomeric tube or bellows is preferably non-conductive and may be made of various materials, e.g. plastic. In an alternative configuration, the tube or bellows may be made from a conductive material and an insulating material may be located between the tube or bellows 24 and one or both of the ring 23 and the electrode 21. An insulating material 115 provides both insulation and clearance from the frame 20. In an alternative embodiment where frame 20 is non-conducting, material 115 may not need to be an insulator. An outlet port or tube 26 provides access to the outside of said assembly. The electrolytic cell assembly is mounted inside an elastomeric sack 25 similar to a balloon, as shown in FIGS. 3a and 3b, so that the sack 25 contains an opening both to the inlet gas port 9 (i.e. port for removing gas during reservoir filling) and the opening 26 from the electrolytic cell. In an alternative embodiment, sack 25 may be replaced with a bellows or other barrier element that separates a first reservoir (containing the fluid to be dispensed) from a second reservoir (containing the generated gas) and allows the size of each reservoir to vary in a complementary manner. Outside the opposite end of the cell, a soft spring 27 keeps a small pressure on the volume contained within the bellows 24 of the electrolytic cell of FIG. 2.

The bellows enclosure 24 of the electrolytic cell 29 is filled with a volume of conducting liquid 28, such as a very dilute saline solution (e.g. NaCl in water). There are other electrolysis fluids that can be used, some that may be more efficient than a saline in water solution. A current is applied by a control circuit and/or a battery 114 as illustrated in FIG. 2. The control circuit makes an electrical connection to ring 23 on the second end of the electrolytic cell and to frame 20. Frame 20 conducts the current to the spring 22 and thence to the electrode plate 21. A current is passed between ring 23 and electrode 21 through conducing liquid 28. The current path from the control circuit or battery 114 to ring 23 and frame 20 is illustrated diagrammatically by the lines 126 and 128 in FIG. 2. In the case of a water-based electrolyte, the current causes breakdown of the water into hydrogen and oxygen gases. These gases then pass though the gas permeable membrane 22 and cause the elastomeric reservoir sack or balloon 25 to expand. The spring 27, in addition to being part of the conducting path, helps to exhaust the gas from the electrolytic cell 29 into space 13. Space 13 is bounded by the reservoir balloon 25 of FIGS. 3a and 3b. The gas is preferably exhausted from cell 29 so as to eliminate gas pockets in the cell that might keep the fluid 28 from being in contact with the electrodes 21 and 23. The reservoir balloon 25 experiences an increase in internal pressure as a result of the increased quantity of gas. This increased pressure causes the volume 13 of balloon 25 to expand until an equilibrium state is reached between external and internal pressures. The expansion of balloon 25 in turn causes a decrease in the volume of fluid reservoir 11 and thus causes fluid to flow out of the reservoir 11 through the exit port 41. The fluid then preferably flows through a filter 50 and a pressure regulator 51 to a catheter 52, and thence into the target region of the body.

In this embodiment, to aid in exhausting gas from cell 29, it is preferred that the membrane 22 be located in a position vertically above the electrolytic solution in the cell 29 during normal orientation of the body part in which the pump is implanted. The implantable pump of this embodiment, when implanted in the torso, is preferentially oriented with the inlet port 1 at the top (towards the person's head) and the exit port 41 and catheter 52 at the bottom (towards the person's feet). This orientation places the membrane 22 at the top so that when the patient's torso is erect, i.e. in a standing or sifting position, this orientation will facilitate gas exhaustion at the top of the electrolytic cell.

Figure 5:
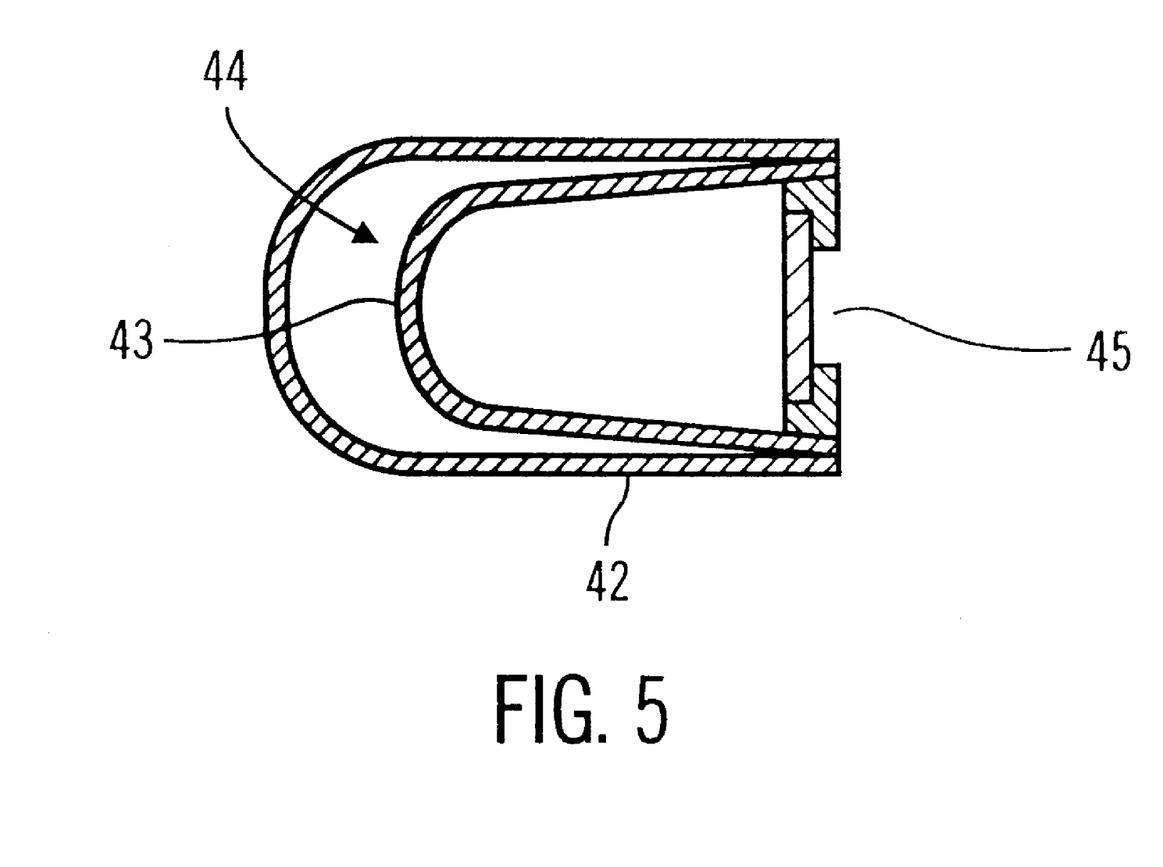
FIG. 5 is an alternate form of an electrolytic cell in another preferred embodiment.

A simpler variation of an electrolytic cell is shown in FIG. 5. In this embodiment a propellant such as FREON is incorporated in the space 44 between a frame 42 and the elastomeric sack 43 to apply pressure on the electrolytic cell instead of by the spring. Of course it may also be sufficient for the electrolytic liquid to be contained in an elastomeric sack that can be extended like a balloon to apply self pressure to the liquid to remove gas through outlet 45 from the solution without any spring, propellant, or other external motivator. Such a self-pressurized sack may also eliminate the need for the frame 42.

Figure 6:
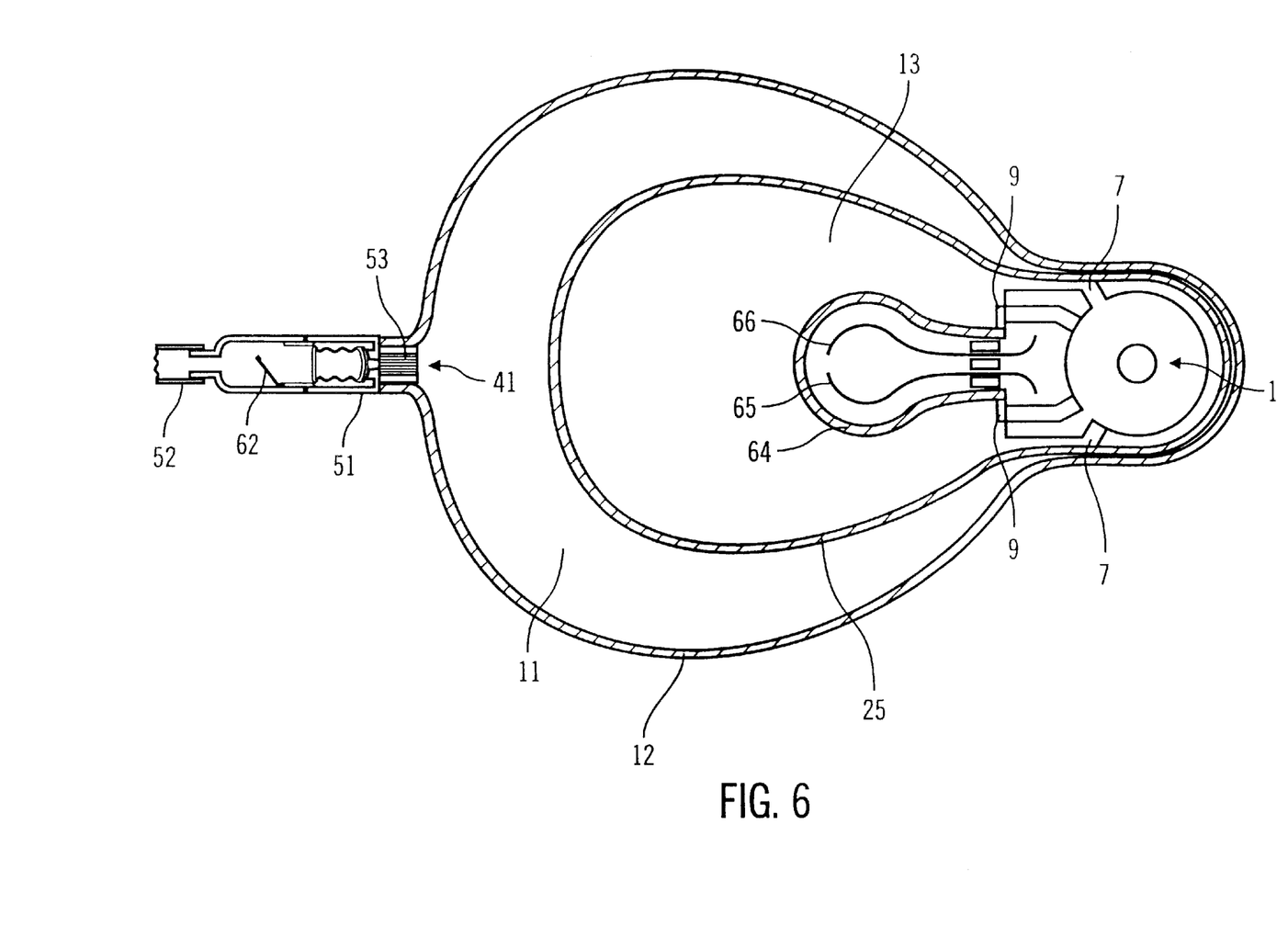
FIG. 6 illustrates an alternative embodiment of a pump using a simplified electrolytic cell.

The elastomeric sack 64 (FIG. 6) of the electrolytic cell, as shown in FIG. 6, may be made from a gas permeable material (i.e. a material that will pass the gas that is generated in the cell but not the liquid). In such a case, the gas may diffuse through sack 64 into the gas or propellant chamber/reservoir 13. A reservoir sack 25 or other barrier device may surround reservoir gas 13 and separate it from reservoir 11. Such a configuration would considerably simplify the connections, etc. Such gas permeable balloon materials could be silicone rubber, or expanded TEFLON (e.g. GORTEX), the amount of porosity (i.e. total open area) determining the maximum transfer rate of the gas between the electrolytic cell and the gas chamber 13. If the gas diffuses slowly, then the electrolytic cell would not empty the gas quickly into the gas chamber 13, thus potentially causing a temporary build up of gas within the electrolytic cell. So long as this temporary gas build up is not so large as to hinder current flow through the liquid between the electrodes this build up will not be problematic since any increased size of cell 29 due to gas retention will still cause an increased pressure within sack 25 that will result in dispensing of fluid from reservoir 11. Once filled with fluid, the only breach to the sack 64 would be for two electrodes 65 and 66 of FIG. 6. Other than to avoid breaking the connecting wires, the sack 64 could essentially be floating within the reservoir balloon 25. Electrodes 65 and 66 are connected to a control circuit (not shown) that provides the electrolyzing current.

In alternative embodiments, the electrolytic cell may not reduce in volume as liquid is converted to gas. The cell may have a fixed volume and the generated gas may be allowed to exit the cell through a permeable membrane or envelop as pressure increases with continued gas production. In a further alternative, the envelope of the cell may be impermeable to gas and it may be designed to expand as the gas is generated. The expansion of the cell results in displacement of some of the reservoir volume originally allocated to the fluid to be dispensed and thus results in the dispensing of material by the pump. A wicking device, such as a hydrophilic sponge material, may be used in these alternative embodiments to ensure that a liquid conduction path exists between the electrodes.

In the above embodiments, the fluid delivery is effected by generating gas and the resultant pressure changes in turn cause volume changes that drive out the fluid through the outlet. The transfer of fluid continues until the pressures in the system are equalized. Except only for losses within the system, other than when a pressure regulator 51 is incorporated, the pressure within the system would equalize to the ambient pressure.

A potential shortcoming with certain embodiments of the invention, as previously noted, involve the fact that changes in ambient pressure can affect delivery. Changes in ambient pressure could stop flow, start flow, increase flow, or decrease flow until pressure equalization occurs. An increase in ambient pressure could cause back flow of body fluids through the catheter 52 and, with a sufficient change in pressure, possibly even into the reservoir 11.

Figure 7:
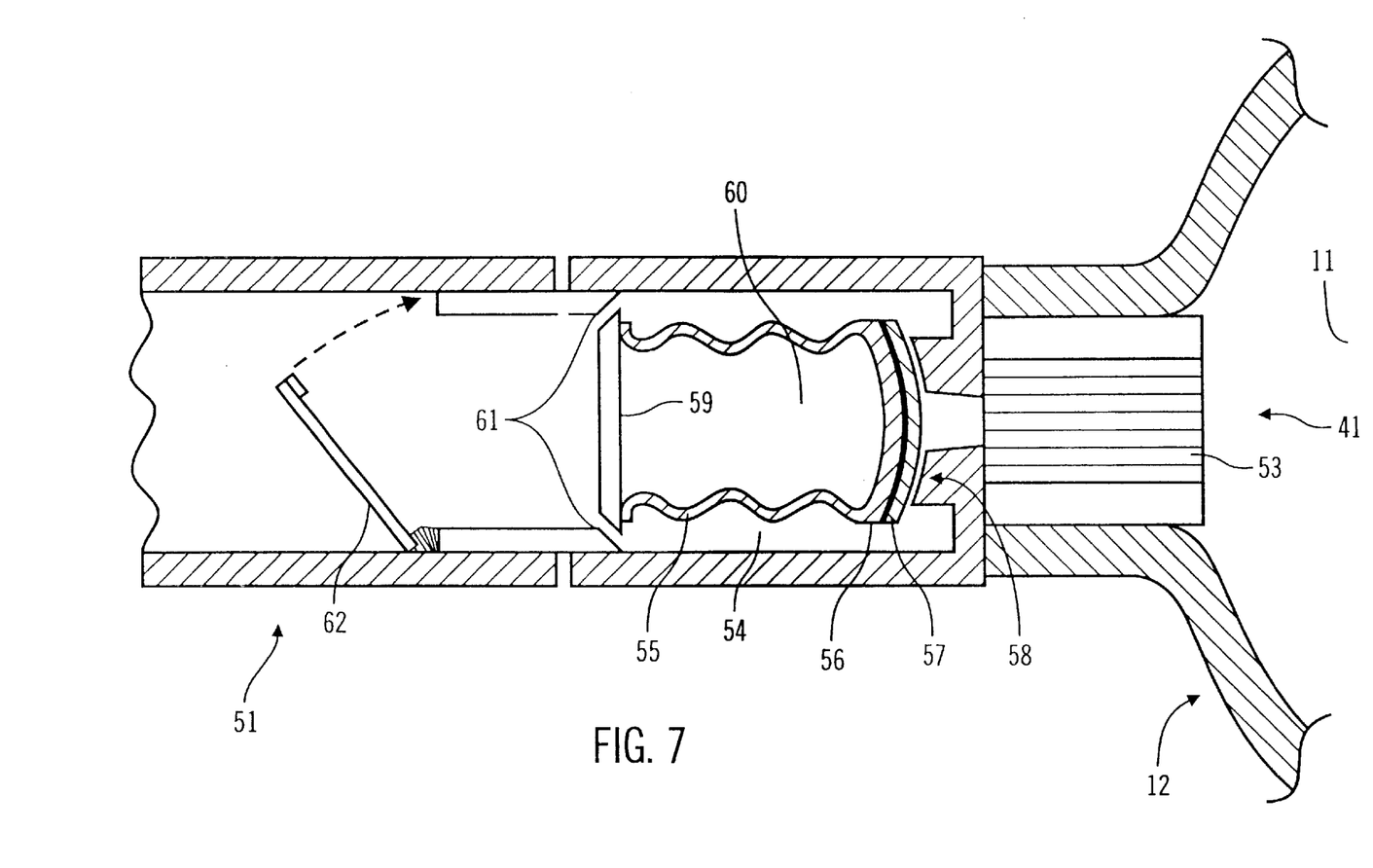
FIG. 7 illustrates a pressure regulator that may be used to minimize negative effects that ambient pressure changes may have on the effective operation of a preferred infusion pump.

FIG. 7 depicts a pressure regulator 51 that may be used in combination with some embodiments to improve a pump's ability to resist the negative influences that ambient pressure change can have on fluid delivery. Pressure regulator 51 may be incorporated at the exit port 41 of the pump to minimize these effects. This regulator is designed to provide a reference pressure above the expected maximum ambient pressure, so that the pump only delivers liquid when the internal pressure exceeds this reference pressure. Such a regulator will maintain the pressure within the pump at the reference pressure, and as gas is generated, expanding the gas chamber 13, the regulator 51 opens and liquid is forced from the reservoir 11 through the outlet until the pressures are again equalized, at which time the pressure regulator inhibits further fluid flow.

However, there is always the possibility that the ambient pressure will exceed the internal pressure as dictated by the pressure regulator, so that as a further back-up for such increased external pressure, a one way valve 62 may provide further protection against back flow. Problems caused by changes in ambient pressure may be minimized when the volume of gas (i.e. compressible and expandable material) in the system is minimized (i.e. the amount of unwanted flow depends on the amount of internal gas within the volume 13). Thus, this problem could be minimized if the reservoir 11 is filled with liquid infusant and the gas is removed from the gas chamber 13 before undertaking activities that would be accompanied by extreme pressure changes, e.g. flying, scuba diving, and changing elevations, and the like.

A given amount of current will generate a fixed quantity of gas (e.g. a given pulse of gas). The increase in pressure created by a given amount of control energy within the gas chamber depends on the pressure and volume of gas present at that time. The fuller the fluid reservoir (i.e. the less volume already occupied by gas within chamber 13), the greater the increase in pressure for a given pulse (i.e. quantity) of gas created. To minimize any impact on the flow rate that may result from varying levels of reservoir volume, the pressure-regulating valve preferably has a high compliance so that it will open and close sharply with a tiny change in internal pressure. As such, it is preferred that only a small difference between activation threshold and deactivation threshold exist.

The preferred maximum difference between activation threshold and deactivation threshold is such that a desired dispensing resolution (i.e. quantity of fluid per pulse) is achievable for the entire range of gas chamber volumes that may be present during dispensing. This desired dispensing resolution for an active material in the fluid being dispensed may be ensured by appropriately balancing the maximum gas chamber volume, the pressure difference between activation and deactivation, and the concentration of active material in the fluid that is being dispensed. Of course, in embodiments where the concentration of active material is lower, more frequent refills may be necessary, more frequent recharging of batteries may be required, and/or a larger quantity of electrolytic fluid may be required.

A preferred embodiment of a pressure regulator is shown in FIG. 7. Fluid flows out of the outlet 41 of the reservoir 11, through an outlet filter 53. Filter 53 filters out any particulate matter that might otherwise pass onto the patient. By proper choice of materials, the filter may also inhibit passage of gas bubbles. After passing through the filter, the fluid moves to the pressure regulator 51. The case of the regulator contains within it a bellows or elastomeric sack 55 with a hard end surface 56 covered with a sealing material 57 (e.g. silicone or bromobutyl rubber) at the sealing end. The other end of this bellows 55 is sealed with a base (distal) plate 59, forming an air or gas chamber 60. This chamber 60 is filled with gas at a pressure that is slightly above the anticipated maximum ambient pressure limit that will be encountered. For example, the pressure might be set between 1.05 and 1.2 standard atmospheres (e.g. 1.1 atmospheres) or more.

When filled, assuming the internal pressure within chamber 11 is below the pressure of reference chamber 60, the bellows 55 expands to cause the sealing material 57 (e.g. elastomeric surface) over the hard end surface 56 (i.e. valve surface) to seat against the valve seat 58. At ambient pressures above that of the internal reference chamber 60, proper seating will not occur and the valve will not operate effectively. The base plate 59 has holes 61 outside the area of the gas chamber 60 to permit fluid to pass out of the regulator. Thus, when the external ambient pressure and the internal pressure in reservoir 11 are lower than the preset pressure in the gas chamber 60, the valve is sealed and no fluid is pumped. The device acts as a regulator that only allows fluid flow when the internal pressure rises to or slightly above the preset reference pressure level in chamber 60. As noted above, it is desirable for the compliance of the bellows to be high so that its spring constant does not adversely affect the opening or closing of the valve. If the compliance is not sufficiently high, dispensing accuracy of the system might be affected particularly as volume of gas within the gas chamber 13 increases.

As an example, if the gas pressure in the chamber 60 is put at 1.2 standard atmospheres, this system would protect against excessive delivery in virtually all normal environmental exposures, including swimming at depths under less than about 6 feet of water. As noted above, a problem could still arise if the ambient pressure should increase beyond the 1.2 standard atmospheres. Without other protection such an increase in pressure may cause the pressure regulator 51 to open and body fluid to be drawn into catheter 52, pressure regulator 51 or even reservoir 11. The extent that body fluids are drawn into the system depends on how much compression of bellows 60 and the gas within the gas chamber 13 is necessary to cause their pressures to reach the level of the high ambient pressure. Thus a safety problem may occur in scuba diving or other environments where ambient pressures may exceed the chamber pressure.

To minimize risks associate with environments that exceed the regulator pressures, a one-way pressure valve 62 may be located at the outlet of the system so that fluid may not flow backward through the catheter. Additionally, to minimize this risk, a patient may be advised to have the pump completely refilled prior to being exposed to such environments. Since the safety of the system is dependent on the performance of the regulator valve 51, the safety of the system could be improved with redundancy by incorporating two such pressure regulators in series.

In alternative embodiments, with or without the use of a pressure regulator, a pressure sensor could be incorporated in the system to sense changes in ambient pressure. In this way, detected changes in pressure could be used to adjust the electrolysis current supplied to the cell by the control circuit to at least partially compensate for the impact that pressure has on fluid delivery. In other alternatives the system may have a pressure sensor to detect pressure build up inside the pump. Excess pressure inside the pump may signal that a blocked catheter or other malfunction exists. Additionally, the system may send a warning when the ambient pressure exceeds the reference pressure of chamber 60 or when excess pressure inside the pump is detected.

The amount of liquid required for electrolysis is extremely small compared to the volume of fluid dispensed by the pump. For an electrolyzing fluid of water, the amount of electrolyzing fluid needed to empty fluid reservoir 11 is less than $\frac{1}{1,250}$ of the reservoir capacity at STP (i.e. less than 18 grams per mole of water/22,400 ml per mole of gas at STP). The above is a conservative estimate of volume of gas produced from the electrolysis of water as a mole of water actually produces 1.5 moles of gas. As such, the calculations to follow may be considered to yield a conservative result with regard to size and energy needs.

If we want a reservoir 11 of 30 ml capacity, and if it is to be refilled every 30 days, and at least 120 refills are desired so that the system may operate without refilling the electrolytic cell for ten years, and a pressure regulator is used and set at 1.2 atmospheres, then the volume of electrolyzing fluid needed in the electrolysis cell is less than $120 \times 1.2 \times 30 \times \frac{1}{1,250}$ or about 3.5 ml. A little extra electrolyzing fluid may be desired to ensure that the electrodes are always in fluid.

In alternative embodiments, instead of starting with an electrolytic cell containing sufficient liquid to last the life of the pump, fresh liquid could be added to the cell in much the same manner that the reservoir of fluid is periodically refilled and the generated gas is removed. This alternative adds more complexity to the system but adds the minor advantage of a slight reduction in size as well as the ability to flush out old electrolyte from the system that may be contaminated by some of the infusant that may diffuse through the reservoir sack 25 during the projected life of the system.

Other embodiments may be based on different assumptions and design criteria.

Figure 8:
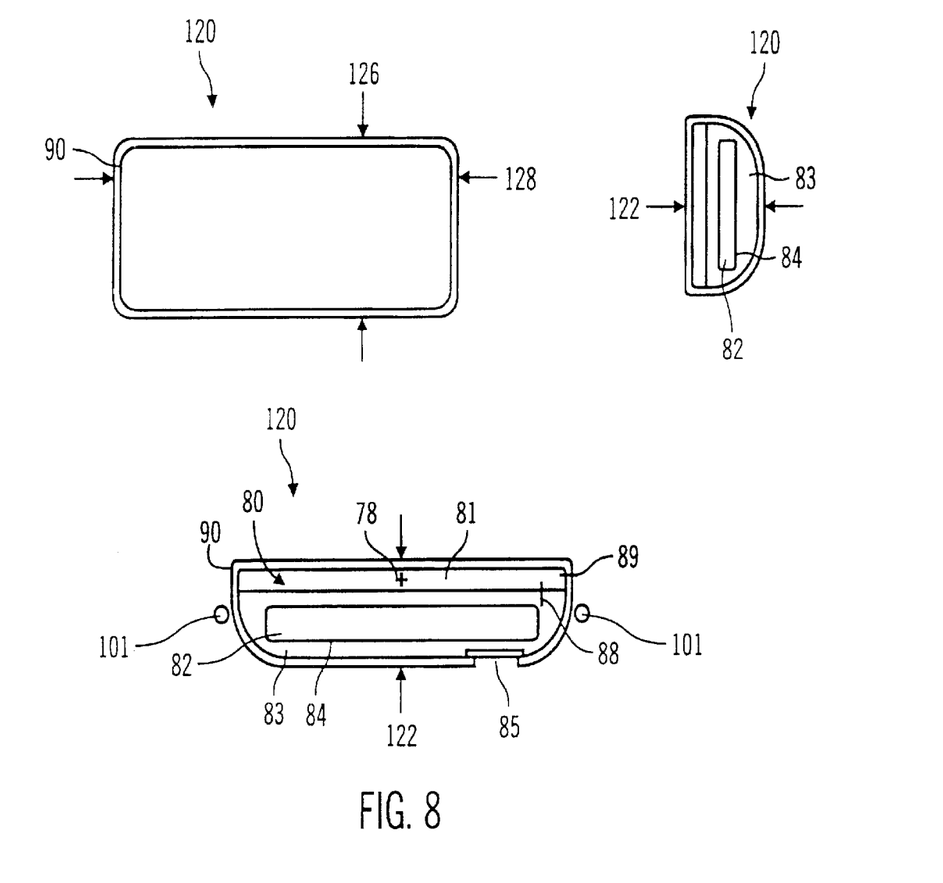
FIG. 8 illustrates an assembly of a preferred configuration of a battery, hybridized electrical control circuit and another alternative form of an electrolytic cell.
Figure 9A:
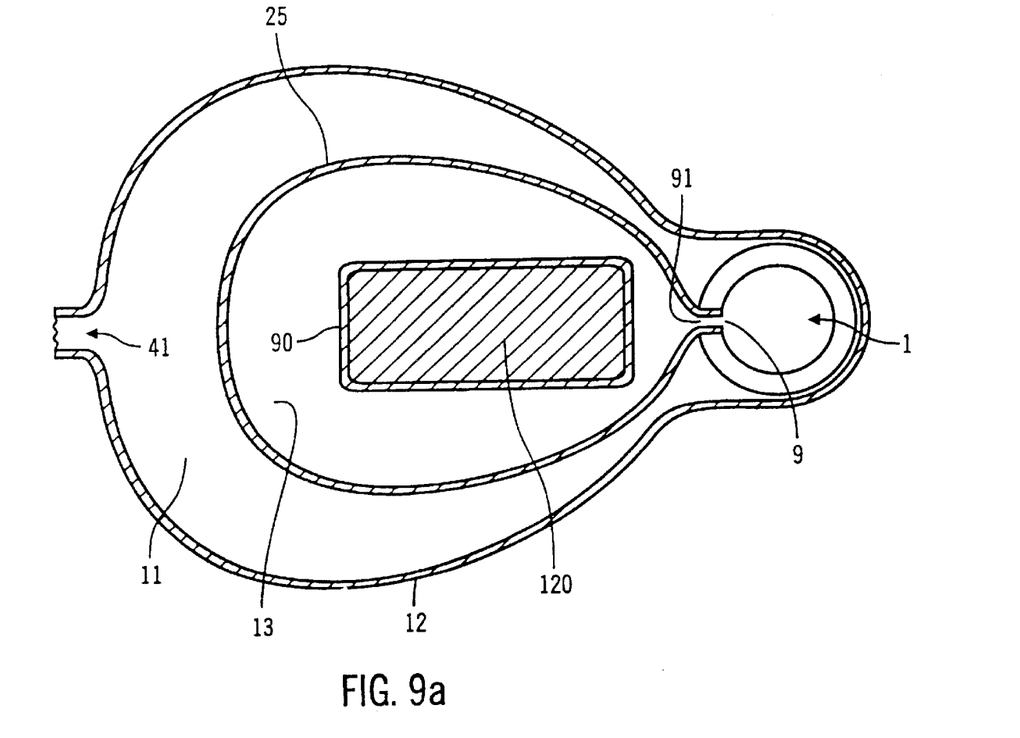
FIGS. 9a and 9b illustrate a preferred embodiment of a pump assembly incorporating the assembly of FIG. 8.
Figure 9B:
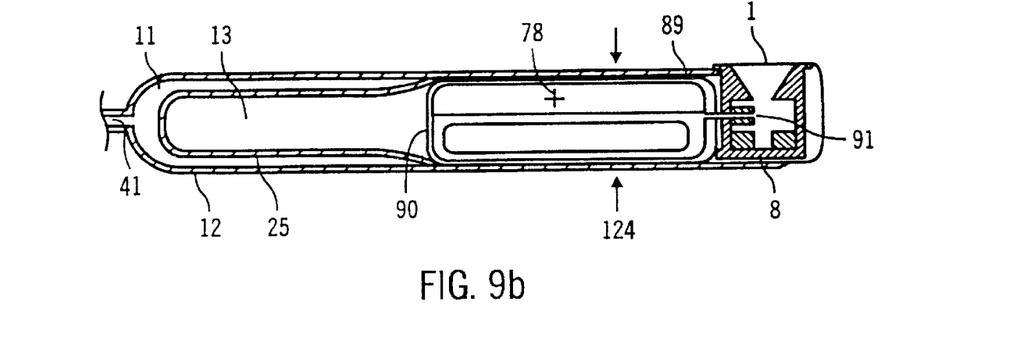

Electrical power is needed to effect the electrolysis and to power the control circuit. Power sources and control circuitry are generally known to those of skill in the art. A preferred embodiment of a control circuit, a rechargeable battery and a recharging coil in an assembly are shown in FIGS. 8, 9a and 9b along with a propellant chamber 82.

Electrolysis of water requires about 1 mah of energy at 1.2 volts to generate 1 ml of mixed hydrogen and oxygen at standard temperature and pressure ("STP"), or 1.2 mah at 1.2 atmospheres. Thus, to deliver 1 ml/day of drug with the pressure regulator at 1.2 atmospheres will require about 1.2 mah at 1.2 volts, or 36 mah/month. Adding 5 $\mu$a or 3.6 mah per month for the circuit housekeeping to the 36 mah per month at 1.2 volts for fluid delivery would yield a total of about 39.6 mah at 1.2 volts per month.

If a lithium iodine primary battery is used and a ten year life is desired, assuming a battery voltage over the ten years of about 2.4 volts and 80% efficiency in the circuitry, the battery capacity would have to be $1.25 \times 120 \times 39.6 \times 1.2/2.4$ or about 3 ampere hours. Such a battery would be relatively large and thus not preferable. Thus, for a desired life of more than a few years it would be preferable to use a rechargeable battery such as a nickel metal hydride battery, lithium ion battery, lithium polymer battery, or other form of battery with periodic recharging.

If a lithium ion rechargeable technology is used, current batteries may deliver about 67 to 69 mah per cc (based on 240–250 mwh/cc) at 3.6 volts. To provide long battery life, it is best to deplete only about ⅓ of the battery capacity during discharge, so if it is assumed that 40 mah is required at 1.2 volts, then the battery should be sized at about 120 mah at 1.2 volts. Assuming 80% efficiency to convert from 3.6 v to 1.2 v, the battery needs to have a capacity of about $(1.25) \times (1.2/3.6) \times 120 = 50$ mah at 3.6 v. At 67 mah per cc, the minimum battery size is about 0.75 cc. By way of example, if the battery covers the flat portion of the bottom of the pump housing of FIG. 3, and if that area is just 5 cm in diameter, the battery thickness would be less than one-half mm, as shown with reference numeral 100 of FIG. 3b. One skilled in the art may derive other battery capacities and configurations based on other assumptions and design criteria.

Since the reservoir must be refilled periodically, e.g. monthly, the battery may be recharged at the same time. Recharging may occur, for example, through radio frequency telemetry or directly via electrical contacts. In the latter case, one contact may be made to the stop 8 by passing the needle through the insulating rubber septums of the inlet port. The other contact may be to any spot on the metal case. The first contact could utilize needle 31 that passes through the septums 3 and 5 to the stop 8. In this case the outer surface of the needle 31 could be coated over the area that would be exposed to body fluids with an insulating coating 38 such as TEFLON, ceramic, epoxy, or any other insulating material that does not adversely interact with the body. Stop 8 may act as an electrical contact for the needle. Stop 8 must then be electrically insulated from the case of the pump and the contact may be connected to one pole of the battery. The outer case 12 of the pump may be connected to the other pole of the battery. If the recharging is done by telemetry, it would be preferable for the battery charge control to be part of the pump electronics, whereas if it is done by conduction as described here, the necessary circuitry could be outside the pump and the body.

The electrical control circuit may store a profiled delivery program that may be downloaded from outside the body. This program may be downloaded using the same connection means as the recharging, i.e. using two needles, one through the inlet port and the other to the case. If the patient is to have control over the program, as for example to control a bolus delivery, the needle insertion for downloading the program would seem to be impractical. It may be done more easily either by r.f., induction, or with a magnet. If by r.f., a receiving coil may be used for recharging the battery, downloading a program of basic control and any patient control. As the program loading and battery charging functions are not intimately linked, different approaches to each may also be used. Although the direct recharging system would be very simple and very efficient, the recharging procedure, at a charge rate of C (e.g. 0.08–0.12 ma), may require about M minutes (e.g. 20–30 minutes) per session assuming a depletion of about 40 mah. If having the two needles connected for 20–30 minutes once monthly with sufficient pressure to assure contact is considered too difficult, then r.f. charging may be used. This embodiment would be much less efficient, would require a receiving coil and charge control circuitry inside the device and a charge system with telemetry outside the body.

An alternative system may involve the use of direct contact recharging (e.g. by needles) and r.f. recharging. R.f. recharging may be used periodically between refills thus reducing the time required for recharging using direct contact (e.g. as part of a refilling procedure).

Since the power from the battery is used both for powering the control system as well as for electrolysis, and since these functions are primarily involved in operating the electrolytic cell, still another embodiment of the invention may combine the electrolytic cell, the control circuit and the battery in single assembly 120, as shown in three orthogonal views of FIG. 8. This configuration simplifies the interconnections and the assembly. In one embodiment, the battery and the circuit may be laid against opposite sides of a flat electrolytic cell, and in another, the battery and circuit may be in located on the same side of the electrolytic cell, depending on how much area is required for the circuit. The latter configuration is illustrated in FIG. 8.

Typically a conventional hybrid circuit requires a height of about 3 mm, although new techniques for hermetic circuit assembly can be much thinner. For the configuration as illustrated, conventional hybrid circuit assembly is illustrated with reference numeral 81 in FIG. 8. Since, in this example, about 4–5 ml of electrolytic fluid are desired (i.e. somewhat more than the 3.5 ml amount estimated previously) and with a cross-section area for the assembly having a width 126 of 2 cm and a length 128 of 3.5 cm, or 7 cm$^2$, the electrolytic cell would have an inside height of about 7 mm to incorporate 5 ml of liquid. This in turn corresponds to an outside height of 7.5 mm when a 0.25 mm wall thickness is used. This places the height 122 of assembly 120 of FIG. 8 at about 10.5 mm, and with the reservoir sack made of 0.125 mm material and a wall thickness of the case 12 at 0.25 mm, the total height 124 of the pump of FIG. 9 is approximately 11.25 mm. With an inside height of about 10.75 mm and allowing 7 cm$^2$ of area for the assembly 120, and if the reservoir sack 25 is made of 0.125 mil material, to provide for a reservoir 11 holding 30 ml of fluid would require a cross sectional area of approximately $37/1.05 = 35¼$ cm$^2$. This translates into a round reservoir having a diameter of about 6.7 cm. Allowing for a round edges to minimize erosion of body tissue by the implanted pump, the reservoir would be about 7.5 cm in diameter.

Since we would like 0.75 to 1 cm$^3$ Of battery volume, with a 3 mm thickness and 2 cm width, a battery length of about 1.5 cm would be sufficient. Thus leaving a 2 cm×2 cm area for the circuit. Naturally these dimensions can all be adjusted to effect the most effective packaging. Assuming all this to be sufficient, a possible configuration of the internal assembly of electrolytic cell, circuit and battery are shown in FIG. 8.

In FIG. 8, the battery 80 couples to the control circuit 81 with a feedthrough for one pole of the battery shown at 78.

The metal enclosure acts as the second pole. The control circuit 81 then determines the current to be provided for electrolysis according to a preset program or a programming command, and that current is then applied between the feedthrough/electrode 88 and the case. The electrolytic fluid is contained in the space 83. The current generates gas in this liquid space 83, and the gas passes through the membrane 85 which would be moved to the end or side of the cell rather than on the bottom. To facilitate the gas diffusion, a sack 84 encloses a propellant such as FREON in the space 82 exerting a small pressure on the liquid that is slightly higher than the reference pressure of the pressure regulator 51. The sack 84 must be configured so that the electrode 88 is always within the electrolytic fluid.

Assuming there is no need to replenish the liquid in 83, the only interfaces needed with the assembly of FIG. 8 are for recharging the battery and for programming the circuit. As described previously, the recharging can be effected at the time of reservoir refilling by simply passing the recharging current between a needle in contact with the contact plate 8 in the inlet port 1 of FIG. 1 and the case 12, with a conducting path to the case of the gas chamber 90 of the assembly 120 in FIG. 8. Because it is desirable that no current be applied across the human body, the exterior of the body of the refill needle 31 is preferably insulated with a material 38 as depicted in FIG. 4. Alternatively, two special insulated needles could be used, with insulation except at the tip and they could incorporate springs in the conducting path or other devices so that contact to the metal parts 8 and 12 may be more easily maintained. For recharging by conduction, two wires must be passed through an opening 91 of the reservoir sack 25 assuming that the reservoir sack completely surrounds assembly 120. One of the wires is connected from the outside to the charge control circuit in the electronic package through the feedthrough 89 and the other is connected to the case 90 of the assembly 120 from the outer case 12 of the pump in FIG. 9.

As noted above, still another possible recharge means would use r.f, telemetry, with an external charger sending the power by telemetry to a coil on the inside of the assembly. An advantage of the r.f. system is that the receiving coil can be inside or around the assembly 120 with no wires passing outside the reservoir sack 25. A possible problem is that with all the metal surrounding the receiving coil, the r.f. will be less efficient and there will be heating of the system due to these losses. If the conductivity of the metals is so high at the telemetry frequencies that are used, the coil could be moved outside or to a face of the pump and a ferrite core could be incorporated with the coil to increase efficiency.

The electrolysis cell generates gas as in the earlier described embodiment. The assembly of FIG. 8 is all contained within the reservoir sack 25. Thus, other than the connections described in the prior paragraph, the only communication from the gas chamber space 13 to the outside is through the port 9 in the inlet port 1 and then to the outer lumen in the needle 31, that is used for exhausting the gas from the space 13. Any necessary wires for recharging and programming the pump may also pass through that tube 91.

A health care professional, pump manufacturer, distributor of the pump system, or even the end user may be able to program the system using the needles or r.f. telemetry as described above for recharging the battery. For example, the recharging can be done with direct current to the needles or some low frequency r.f. signal. R.f. programming can be done with a signal having a frequency significantly higher than that of the recharging signal, and the internal circuit can then identify and separate the two types of signals.

Although possible, use of the needles by a patient to provide real time changes to the program is not desirable. For patient programming, an r.f. receiver would be preferable to receive signals from an external programmer. Such a system would be desirable for complex programming needs, e.g. titrating an insulin delivery profile for a Type I diabetic. For such an r.f. system, a receiving coil 101 is preferred.

In an alternative embodiment a simpler system, especially useful for limited commands such as delivering a bolus of morphine for relief of pain, may utilize a reed switch in the control circuit and an external permanent magnet or electromagnet. Such a system could also provide some variable control by having the reed switch operate a stepping switch, using a magnet placed near the pump (or reversing it again and again), each step changing the delivery by a fixed amount. Such a system could be used to step the delivery up or down.

In FIG. 9*a* the outer case 12 contains the reservoir 11 that is bound on the inside by the reservoir sack 25. Inside the reservoir sack 25 is gas chamber 13 that contains the electrolysis cell/control circuit/battery assembly 90. Through a single opening 91 in the reservoir sack 25 a tube passes for exhausting the gas during the refilling process, and through this hole also pass the two wires used for recharging the battery if by conduction and, if so implemented, for programming the control circuit.

As described, the assembly 90 essentially fills the space within the reservoir sack in that area of the system, providing support between the top and bottom of the case 12. If the shape of the assembly 120 can be made to enable the sack 25 to readily close around it when the reservoir is full then it would be desirable to bond the case 90 of the assembly 120 to the material of the reservoir sack 25. If on the other hand it is desired for gas to flow around the internal assembly case 90 (e.g. to allow access to membrane 85 or opening 91), small silicone rubber discs, lines, or the like may be placed between the reservoir sack 25 and the case 90. To avoid stagnation and to provide liquid flow between the reservoir sack 25 and the outer case 12 in the area around assembly 120, some ridges could also be incorporated into the outer case to enable flow; however, it may be desirable instead to bond the case 90 to the reservoir sack (25) with or without reservoir sack (25) being bonded to assembly 120 so there is no flow and no trapping of fluids in these regions. This would also help to stabilize the position of the internal assembly.

While particular preferred embodiments of the present invention have been described above, it will be understood by those skilled in the art that many modifications and variations of the teachings may be made without departing from the spirit of those teachings. For example, other liquids or solids may be used as a source for generating the gas that provides the motive force for expelling the desired material from the pump to the living body. In some embodiments it may be possible to use the selectively mixing of two chemicals to produce the gas.

In still other embodiments, it may be possible to increase the pressure inside the pressure regulator when increased ambient pressure is detected (by a sensor in the implantable device) and to cause the gas generation system to operate to bring the internal pressure in the regulator up to the new pressure. The increase in regulator pressure may be obtained by directing a portion of the generated gas to the pressure regulator bellows. In face of the increased regulator pressure, an appropriately programmed control circuit may decide on the quantity of gas to generate to achieve a desired infusion amount. When ambient pressure is determined to have dropped, the pressure regulator may still continue to operate under the increased pressure until refilling occurs or alternatively it may be decreased in a controlled manner as material is intended to be infused. The pressure in the regulator may be decreased by feeding it back into the second reservoir. The directing of gas into and out of the pressure regulator bellows may be accomplished by an appropriate combination of valves (e.g. normally closed but temporarily openable) and pressured based seals.

In still additional embodiments, instead of expelling the gas from the second reservoir at the time of refilling, it may be possible to convert the gas back into a liquid such as by applying one or more sparks to hydrogen and oxygen gas, or the like, when such products exist as a result of pump operation. As water occupies far less volume that than does the gas, it may be acceptable to allow the small amounts of water to build up in the second reservoir.

In view of the embodiments presented, the alternatives presented above, and in view of the various alternatives that will be apparent to those of skill in the art upon review of the instant teachings, it is intended that the scope of the invention be set by the appended claims and any range of equivalency associated therewith.

What is claimed is:

1. An implantable infusion pump for dispensing a fluid to a patent, comprising:
    a pump housing capable of being implanted in a body of a patient;
    an inlet in the housing for receiving the fluid to be dispensed, the inlet in the housing including a first septum and a second septum;
    an outlet in the housing from which fluid is dispensed;
    a first reservoir of variable size for holding the fluid, wherein the inlet and first reservoir are connected at least periodically by a flow path so as to allow fluid supplied to the inlet to flow to the first reservoir, and wherein the outlet and first reservoir are at least periodically connected by a flow path so as to allow fluid in the first reservoir to be dispensed through the outlet;
    a second reservoir of variable size for holding a gas;
    a volume comprising the first reservoir and the second reservoir, such that as the second reservoir expands in size the first reservoir diminishes in size; and
    a gas generating source for controllably and variably producing quantities of gas that expand the size of the second reservoir, thereby decreasing the size of the first reservoir to cause dispensing of fluid through the outlet to the patient.

2. The pump of claim 1 wherein the source for generating gas comprises a controllable reaction trigger for causing at least a first chemical substance to change into at least one secondary chemical substance wherein at least one of the secondary substances comprises a gas.

3. The pump of claim 2 wherein the reaction trigger comprises an electric current.

4. The pump of claim 3 wherein the at least first chemical substance comprises a conducting solution that comprises water.

5. The pump of claim 4 wherein the conducting solution comprises NaCl.

6. The pump of claim 4 wherein the at least one secondary chemical substance is a gas of hydrogen and a gas of oxygen.

7. The pump of claim 6 wherein the reaction trigger converts water to gases of hydrogen and oxygen by electrolysis.

8. The pump of claim 2 wherein the reaction trigger causes a liquid substance within a reaction chamber to create a gas, and wherein the reaction chamber is separated from the second reservoir by a membrane that is permeable to a generated gas but is relatively impermeable to the liquid from which the gas is generated.

9. The pump of claim 8 wherein the reaction chamber is contained within a volume of variable size, such that as gas is created and passes through the membrane the chamber reduces in size so that the reaction chamber contains primarily liquid.

10. The pump of claim 2 wherein the reaction trigger causes a liquid substance to create a gas.

11. The pump of claim 1 additionally comprising a pressure regulator located along the flow path between the first reservoir and the outlet.

12. The pump of claim 11 wherein the pressure regulator inhibits flow of fluid to the outlet when a pressure of the gas in the second reservoir is less than a preset amount.

13. The pump of claim 12 wherein the preset amount is at least 1.1 standard atmospheres.

14. The pump of claim 13 wherein the preset amount is at least 1.2 standard atmospheres.

15. The pump of claim 11 wherein the pressure regulator comprises:
    a sealed chamber filled with a gas, the sealed chamber having an end surface; and
    a seating surface to which the end surface of the sealed chamber is pressed by the gas in the sealed chamber when the pressure in the second reservoir is less than the pressure in the sealed chamber when the sealed chamber is in contact with the seat;
    wherein the end surface is dislodged from the seat, and fluid is allowed to flow through the outlet, when the pressure within the second reservoir exceeds the pressure within the sealed chamber.

16. The pump of claim 11 wherein a one-way valve is located between the regulator and the outlet.

17. The pump of claim 11 wherein a filter is located between the first reservoir and the pressure regulator.

18. The pump of claim 1 additionally comprising a filter located between the first reservoir and the outlet.

19. The pump of claim 1 additionally comprising a one-way valve between the first reservoir and the outlet.

20. The pump of claim 1 wherein the inlet comprises:
    a guide region; and
    a stop;
    wherein the first septum is located between the guide region and the second septum, and the second septum is located between the first septum and the stop;
    wherein a first inlet is between the first and second septums and a second inlet is between the second septum and the stop, and
    wherein one of the first inlet and the second inlet allows fluid to be added to the first reservoir, while the other inlet allows gas to be exhausted from the second reservoir.

21. The pump of claim 1 wherein the gas generating source comprises an electrical control circuit and a battery.

22. The pump of claim 21 wherein the battery is rechargeable while implanted in the body by one or both of (1) conduction from a source outside the body through at least one lead that is made to contact the pump, and (2) r.f. energy transfer from a source outside the body.

23. The pump of claim 1 wherein a first and second inlet are provided for accepting a first and second syringes that may be used for adding fluid to the first reservoir and for exhausting gas from the second reservoir, respectively.

24. A method for infusing a fluid into a body of a patient, comprising:

providing an implantable device in a patient, wherein the implantable device includes a volume that is partitioned into a first reservoir of variable size and a second reservoir of variable size, such that as the second reservoir expands in size the first reservoir diminishes in size;

providing fluid to a first reservoir; and generating and providing within the implantable device quantities of a gas, on a controllable and variable basis, to the second reservoir to cause expansion of the second reservoir such that a portion of a volume of the first reservoir is diminished and a portion of the fluid supplied to the first reservoir is dispensed through an outlet of the implanted device into the body of the patient;

providing a first septum within the implantable device;

providing a second septum with the implantable device; and wherein a first inlet is between the first and second septums and a second inlet is between the second septum and a housing of the implantable device, and wherein one of the first inlet and the second inlet allows fluid to be added to the first reservoir, while the other inlet allows gas to be exhausted from the second reservoir.

25. The method of claim 24 wherein generating a gas comprises causing at least a first chemical substance to change into at least one secondary chemical substance, wherein at least one of the secondary substances is a gas.

26. The method of claim 25 wherein causing comprises applying an electric current to the first chemical substance.

27. The method of claim 26 wherein the first chemical substance comprises water.

28. The method of claim 27 wherein the at least one secondary chemical substance is a gas of hydrogen and a gas of oxygen.

29. The method of claim 24 additionally comprising:

allowing fluid to enter the body of the patient only when a pressure within the second reservoir exceeds a preset amount set by a pressure regulator located along the flow path between the first reservoir and the outlet.

30. The method of claim 29 wherein the preset amount is at least 1.1 standard atmospheres.

31. The method of claim 30 wherein the preset amount is at least 1.2 standard atmospheres.

32. The method of claim 29 wherein a one-way valve is located between the regulator and the outlet.

33. The method of claim 29 wherein a filter is located between the first reservoir and the pressure regulator.

34. The method of claim 24 wherein the generating of a gas comprises utilization of an electrical control circuit and a battery.

35. The method of claim 34 wherein the battery is recharged while implanted in the body by one or both of (1) providing charging current through a conducting element extending from a source outside the body to the pump, and (2) supplying r.f. energy to the implanted device from a source outside the body.

36. An implantable device for dispensing a drug to a patient, comprising:

a means for holding a fluid that may be electrolyzed, a means for causing a selected amount of the fluid to be electrolyzed to produce a gas;

a means for separating produced gas from the fluid and allowing the gas, but not the fluid, to pass to a volume surrounded by a variable size containment means;

a reservoir means for holding a drug to be dispensed, the reservoir means being of variable size and located in relation to the containment means such that as the containment means increases in size, the reservoir means decreases in size thereby dispensing the drug to the patient;

a means for refilling the reservoir with the drug; and a means to remove gas from inside the containment means so that refilling of the reservoir means may occur;

a first septum located within the implantable device;

a second septum located within the implantable device; and wherein a first inlet exists between the first and second septums and a second inlet exists between the second septum and a housing of the implantable device, and wherein one of the first inlet and the second inlet allows fluid to be added to the first reservoir, while the other inlet allows gas to be exhausted from the second reservoir.

37. The device of claim 36 wherein the means to remove gas comprises an outlet means to exhaust gas from inside the containment means.

38. The device of claim 37 where the outlet means is opened to allow exhaustion of gas when the reservoir means is meaning refilled.

39. The pump of claim 20, wherein the guide region is conical.

40. An implantable device comprising:

a housing;

a first reservoir located within the housing for holding fluid;

a second reservoir located within the housing for holding gas;

a first septum located within the housing; and a second septum located within the housing adjacent the first septum, wherein the first septum and the second septum form a first cavity therebetween for allowing fluid to flow from the first reservoir, and the second septum and the housing form a second cavity therebetween for allowing gas to flow from the second reservoir.

* * * * *